United States Patent
Choi (10) Patent No.: US 9,993,513 B2
(45) Date of Patent: Jun. 12, 2018

(54) PREPARATION MADE FROM OATMEAL AND METHOD FOR ITS USE

(71) Applicant: CARICOL—DIGESTIVE & IMMUNE HEALTH GMBH, Wienerwald/Grub (AT)

(72) Inventor: Danette Vanessa Choi, Mountain View, HI (US)

(73) Assignee: CARICOL—DIGESTIVE & IMMUNE HEALTH GMBH, Wienerwald (AT)

( * ) Notice: Subject to any disclaimer, the term of this patent is extended or adjusted under 35 U.S.C. 154(b) by 0 days. days.

(21) Appl. No.: 15/303,523

(22) PCT Filed: Apr. 17, 2015

(86) PCT No.: PCT/IB2015/001205
§ 371 (c)(1),
(2) Date: Nov. 23, 2016

(87) PCT Pub. No.: WO2015/159157
PCT Pub. Date: Oct. 22, 2015

(65) Prior Publication Data
US 2017/0080042 A1    Mar. 23, 2017

(30) Foreign Application Priority Data

Apr. 18, 2014 (EP) .................................... 14165297
Sep. 16, 2014 (EP) .................................... 14184897

(51) Int. Cl.
*A61K 36/899* (2006.01)
*A61K 36/00* (2006.01)
*A61K 36/185* (2006.01)

(52) U.S. Cl.
CPC .......... *A61K 36/899* (2013.01); *A61K 36/185* (2013.01)

(58) Field of Classification Search
None
See application file for complete search history.

(56) References Cited

U.S. PATENT DOCUMENTS

| | | | |
|---|---|---|---|
| 1,414,576 A | 5/1922 | Mack | |
| 4,765,981 A | 8/1988 | Joseph | |
| 2005/0042243 A1 | 2/2005 | Redmond et al. | |
| 2006/0188636 A1* | 8/2006 | Choi | A61K 36/185 426/615 |
| 2009/0311376 A1 | 12/2009 | Rao et al. | |
| 2013/0183405 A1 | 7/2013 | Chatel et al. | |

FOREIGN PATENT DOCUMENTS

| | | |
|---|---|---|
| CN | 102406042 A | 4/2012 |
| CN | 102524640 A | 7/2012 |
| CN | 103461439 A | 12/2013 |
| CN | 103519078 A | 1/2014 |
| WO | WO2004047850 A1 | 6/2004 |
| WO | WO2006069390 | 6/2006 |
| WO | WO2010108277 A1 | 9/2010 |
| WO | WO2015159157 A2 | 10/2015 |
| WO | WO2015159157 A3 | 10/2015 |

OTHER PUBLICATIONS

Website document entitled: "Papaya Oatmeal Bread Sticks" (available at http://www.kiipfit.com/papaya-oatmeal-bread-sticks/). Dated Aug. 7, 2014.*
International Search Report of International Appl. No. PCT/IB2015/001205.

* cited by examiner

*Primary Examiner* — Christopher R Tate
*Assistant Examiner* — Russell G Fiebig
(74) *Attorney, Agent, or Firm* — Falati (57) ABSTRACT

A preparation is disclosed, made of, preferably colloidal, oat flour, along with the same for use in the treatment of diseases, further cosmetic methods, comprising the application of the preparation, as well as methods of making the preparation. The preparation is particularly suitable for use in the treatment of irritable or inflammatory conditions, comprising itching, redness, and/or dry or cracked or open or oozing or thickened or inflamed skin or mucous membrane, for external or internal administration, preferably to the skin or mucous membranes, in particular directly at the site of irritated or inflammatory conditions.

5 Claims, 4 Drawing Sheets

Fig. 2

PREPARATION MADE FROM OATMEAL AND METHOD FOR ITS USE

CROSS REFERENCE TO RELATED APPLICATION

This application is the National Phase filing of International Application No. PCT/IB2015/001205, filed Apr. 17, 2015, which claims priority to two European patent applications, European Patent Appl. No. 14165297.4, filed Apr. 18, 2014, and European Patent Appl. No. 14184897.8, filed Sep. 16, 2014. The entire content of each prior application is hereby incorporated by reference.

The invention relates to a preparation made from natural products, in particular for use in the treatment of skin diseases. It further relates to cosmetic methods, comprising the use of the preparation, and methods of making the preparation.

According to epidemiological studies, many patients worldwide suffer from sensitive skin. Disorders, such as dry skin (xeroderma) and dermatitis, including eczema, are common as well. The same holds true for itching, redness, and cracked, open, oozing, or thickened skin. Dermatitis is an inflammatory reaction of the skin that mostly affects the dermis (sclerotic coat). Psoriasis is also associated with chronic inflammatory processes. Sunburn and insect bites, on the other hand, are associated with acute inflammatory processes.

Mucosae can be affected by disorders or diseases as well that are associated with, or suspected to be associated with, inflammatory processes, and the same holds true for the digestive tract, such as in the case of irritable bowel syndrome.

Atopic dermatitis (ICD-10 L20), also called atopic eczema, is a common type of dermatitis. It is a chronic skin disease that is associated with inflammatory processes (Leung et al., *JCI* 2004, PMID: 14991059). Symptoms include eczema on the skin and severe itching. The lifetime prevalence of atopic dermatitis is 10-20% in children and 1-3% in adults, with the prevalence having nearly tripled in recent decades in industrialized countries.

Although the disease is considered incurable, it is treatable. Common treatments include treating the characteristic skin dryness, for example with moisturizers and/or and the application of anti-inflammatory active agents, usually in the form of ointments or the like, directly to the eczema, the lesion, or the sensitive skin areas that are prone to eczema.

A proven class of drugs in the treatment of atopic dermatitis are corticosteroids for topical use. However, their long-term use is associated with potential side effects and is therefore usually not indicated for the treatment of skin areas without lesions or of less severe manifestations of the disease. Other treatment methods are listed, for example, in the above cited article by Leung et al. and in Akdis et al. (*Allergy* 2006, PMID: 16867052).

The large number of different treatments for atopic dermatitis by itself shows that not every patient can be treated equally for good treatment success. For most patients, a multi-pronged approach is required for effective treatment. Also, in less severe cases, in long-term treatment, or for the mere treatment of itching (e.g., to prevent the adverse "itch-scratch cycle" or to improve the overall well-being of the patient), the administration of drugs, such as corticosteroids or calcineurin inhibitors, is associated with a comparatively high risk in terms of potential side effects. In particular, the suppression of itching could be an effective means to improve the disease pattern.

An object of the present invention is therefore to make a preparation available that firstly provides good efficiency against one or more of the aforementioned symptoms, disorders, or diseases of the skin, at least for a subset of patients. Secondly, the preparation should be suitable for topical application. Furthermore, suitability for use on mucous membranes, e.g. to be used against inflammatory disorders of the mucous membranes or for ingestion in the case of digestive disorders, as well as a improvement of the appearance of the skin as a result of the application would be beneficial.

Moreover, the product should be based on proven natural products, which may increase compliance in many patients due to the often higher acceptance compared to drugs that are not produced from natural products.

In addition, the product should exhibit one or more of the following properties that are advantageous for a commercial product: quality structure that is optimized for the possible applications (e.g., in terms of viscosity and pH), longer shelf life, optionally while maintaining quality structure, and properties that are attractive to the user (with respect to color, odor, taste, consistency, etc.) Viscosity and pH, in particular, are very important to ensure effective application to the skin.

Therefore, the present invention discloses a novel method for manufacturing a preparation of oat flour (that is, a proven natural product), comprising:
  a) suspending the oat flour in preferably cold water;
  b) heating the slurry to boiling temperature with stirring;
  c) boiling the slurry, preferably with stirring, for at least 30 minutes, preferably for at least 45 minutes, more preferably for at least 1 hour, even more preferably for at least 2 hours, most preferably for at least 3 hours;
  the oat flour having a mean particle diameter of less than 2000 µm, preferably less than 1500 µm, more preferably less than 1000 µm, even more preferably less than 500 µm, and most preferably less than 350 µm.

Furthermore, the present invention relates to a preparation obtainable by the method according to the invention. Otherwise, the present invention relates to the above-described preparations for use in the treatment of diseases or disorders. The present invention further relates to cosmetic methods, comprising the application of the preparations according to the invention.

Oat flour is obtained by grinding grains of seed oats (*avena sativa*), a cultivated plant. Oat flour contains nutrients, such as vitamins and minerals, as well as fiber, including beta-glucan, furthermore phytosterols, alkaloids, avenanthramides, silicic acid, and linoleic acid. Preferably, the oat flour used in the present invention is a whole grain oat flour.

Colloidal oat flour can be produced from finely ground oat flour and water and it is contained in various personal care products, such as shampoos, moisturizers, and shaving cream, to protect against skin irritation and dryness of the skin (Criquet et al., Clinical, *Cosmetic and Investigational Dermatalogy* 2012, PMID: 23204849). The positive effects on skin irritation appear to be mediated by the avenanthramides contained in the oat flour, which prevent inflammatory responses. A further advantage of oat flour is that it is not, or only nominally, allergenic.

Avenanthramides are of particular importance for the beneficial effects of oat. Avenanthramides are phenolic substances that are specific to oats. They have been described as anti-oxidative, anti-inflammatory, and anti-atherogenetical (cf., Maria Skoglund, Susanne Bryngelsson, and Lena H.

Dimberg (2003), Enzymes Involved in Changes of Avenanthramide Concentrations in Steeped Oat Grains. In: Future Technologies for Food Production and Future Food Scientists. International Symposium on Future Technologies for Food Production and Future Food Scientists, Gothenburg, Sweden, (90-90). 2-4 Jun. 2003) A further description of avenanthramides can be found, for example, in WO 2010/108277 A1.

In the nomenclature by Collins, a distinction is made, among others, between avenanthramide A, Avenanthramide B, and avenanthramide C (cf., WO 2010/108277 A1, in particular FIG. 2 therein); another nomenclature was established by Dimberg (in which, for example, avenanthramide B is named avenanthramide 2f; Wise, Mitchell L. "Avenanthramides: Chemistry and Biosynthesis." Oats Nutrition and Technology (2013): 195-226). They are all synthesized from precursors present in the oat seed by the enzyme hydroxycinnamoyl-CoA:hydroxyanthranilat N-hydroxycinnamoyl-transferase (HHT)—the concentration of avenanthramide or its precursors may differ, depending on the oats variety and growth conditions. HHT is active during germination. Maceration of intact oat seeds in water the increases the avenanthramide concentration. The optimum conditions for the enzyme activity of HHT, according to Skoglund et al., 2003, are pH 7 and 30° C.

The prior art therefore proposes long maceration in water at temperatures far below the boiling temperature suggested by the invention (e.g., about 100° C. at atmospheric pressure) in order to increase the avenanthramide concentration in the final oats product. For example, WO 2010/108277 A1 recommends maceration in water at a temperature of 4 to 40° C. for 96 to 120 hours (cf., claim 5 of that document). Skoglund et al., 2008, (Skoglund, Maria, et al. "Avenanthramide content and related enzyme activities in oats as affected by steeping and germination." Journal of cereal science 48.2 (2008): 294-303.) also demonstrates an increase in the concentration of avenanthramides that is particularly noteworthy only after 96-120 hours of germination at 16° C. and 20° C., respectively (FIG. 3, ibid).

In the course of the present invention, it has been found, however, that by prolonged boiling, preferably with stirring, (at least 30 minutes)—after brief slurrying—of finely ground oat flour, in particular having an average particle diameter of between 200 µm and 400 µm, an increase in the avenanthramide concentration can be achieved as well. This increase is measured by determining the avenanthramide concentration (e.g., by HPLC, cf., example 4 of the present application as well as WO 2010/108277 A1) in the starting material (oat flour) and in the oat preparation obtained after boiling, each normalized to the respective dry mass, wherein the two concentrations (each specified in ppm, for example) are compared with each other. The method according to the invention allows for such an increase in the (total) avenanthramid concentration by least 10%, preferably by at least 20%, more preferably by at least 50%, most preferably by least 100% (that is, doubling), wherein the avenanthramide B is preferably a component of said (total) avenanthramides, preferably of at least 5%, more preferably at least 10%, even more preferably of at least 20%, most preferably more than 50% or even more than 75%. Referring to example 4 (below), the increase according to the invention of the avenanthramide concentration is demonstrated.

Although some documents are found in the prior art, describing the extended boiling of oatmeal, none of them disclose, however, the prolonged boiling of oatmeal as per the invention, let alone longer boiling for the purpose of increasing the avenanthramide concentration as per the invention. In addition, the word "oatmeal" is ambiguous and can mean both, rolled oats and oat flour. Therefore, any disclosure that uses the word, "oatmeal," without further specification (e.g., by specifying the average particle size), must be regarded as ambiguous in terms of whether it refers to rolled oats or oat flour.

For example, U.S. Pat. No. 1,414,576, disclosed a preparation method for oat products. The boiling time provided is for a period of four to six hours for "dry oatmeal or rolled oats, that is oats from which the hulls have been removed." The term "oatmeal" is not specified in greater detail with respect to the particle size or the degree of grinding. In addition, in the method of U.S. Pat. No. 1,414,576, the oatmeal is not initially slurried in (preferably cold) water as is the case in the method according to the invention. Avenanthramides are not mentioned in the document.

U.S. Pat. No. 4,765,981 describes an extract of oatmeal. The term "oatmeal" is not specified in greater detail with respect to the particle size or the degree of grinding, and the boiling time is at least 1 hour, preferably 3 hours, before extraction by filtration. Avenanthramides are not mentioned in the document.

US 2013/0183405 A1 describes the production of "soluble" oat flour (used for producing oat beverages) used) with increased avenanthramide concentration—when compared to other "soluble" oat flours. Soluble oat flour is prepared by enzymatic digestion of oat flour (e.g., by alpha amylase). During this process, oat flour is heated to achieve starch pregelatinization, whereupon the gelling flour is enzymatically treated (in particular by alpha amylase). Then the enzymatically treated soluble oat flour is extruded with heating. However, the soluble oat flour in this case is neither slurried in water nor subjected to a boiling step, in particular a prolonged boiling step. Furthermore, in the soluble oat flour as described in US 2013/0183405 A1, the maximum achieved increase in avenanthramide 2f (corresponds to avenanthramide B) is only 18.31% (cf., table in paragraph in the document). According to the technical teaching conveyed in the table in paragraph [0064] of US 2013/0183405 A1, this moderate increase of aventhramit content is achieved primarily through a balancing of the amount of enzyme used as well as the optimization of the moisture content of the soluble oat flour and the extrusion step.

With the method according to the invention, however, increases of more than 100% can be achieved (cf. example 4). In addition, the method described in the document requires an extruder, which increased technical complexity. Finally, the object of the present invention is not to provide a soluble oat flour (in which avenanthramides is to be enriched in the course of solubility process), but to provide an improved oat flour product. Hence, according to the method of the present invention, an enzymatic treatment, in particular an enzymatic starch degradation (e.g., by alpha amylases), is not required or provided, and neither is extrusion, in particular heat extrusion. In the method according to the invention, a treatment with enzymes, i.e., addition of enzyme preparations, for example, for the purpose of degradation of starch molecules in the flour, and/or an extrusion step, in particular heat extrusion, is therefore preferably avoided or would even be counterproductive in view of the preferably manufactured products according to the invention.

US 2005/0042243 A1 describes a process for preparing an extract from an oat product ("oatmeal"). The term "oatmeal" is not specified in greater detail with respect to the particle size or the degree of grinding. The method described therein is a solvent extraction without boiling. Unlike in the method according to the invention, while the avenanthramide concentration in the final product was measured, no avenanthramide concentration increase in comparison to the starting material was described.

The aforementioned WO 2010/108277 A1 proposes maceration at 4° C.-40° C., preferably for 96-120 hours, to increase the avenanthramide concentration.

CN 103461439 A, US 2009/311376 A1, and WO 2006/069390 A2 each disclose the preparation of oatmeal, but do not anticipate the present invention, nor could the present invention be derived from them. In particular, none of the documents describes adding a preparation of *carica papaya* fruit (i.e., Component A) to a slurry (containing oat flour) (i.e., Component B).

The use of oat flour (rather than rolled oats) according to the invention allows for a better extraction of the valuable ingredients of the oats and a more homogeneous end product. A homogeneous appearance is very important for both, handling (for example, packaging) and for the consumer, especially when applied to the skin.

In addition, the method according to the invention has the advantage over the prior art that it requires less time and allows for a simultaneous sanitary treatment by holding at boiling temperature.

Oat flour is not only suitable for application to the skin: Oat products, such as oat flour or rolled oats, are digestible and can form an important part of a healthy diet. Their high fiber content can reduce the risk of hypertension, dyslipidemia, and heart disease. In general, individuals with a higher proportion of fiber in their diet suffer from fewer chronic diseases (Slavin, Journal of the American Dietetic Association 2008, PMID: 18953766; abstract). Oatmeal has anti-oxidative and anti-inflammatory properties (Kurtz and Wallo, J Drugs Dermatol 2007, PMID: 17373175; abstract), which can have an alleviating effect on digestive disorders.

Furthermore, an increase in the proportion of oat products in the daily diet can reduce insulin resistance in type 2 diabetes and thereby result in an improvement of the disease pattern. For example, Youn et al (Youn, Moonyeon, A. Saari Csallany, and Daniel D. Gallaher. "Whole grain consumption has a modest effect on the development of diabetes in the Goto-Kakisaki rat." British Journal of Nutrition 107.02 (2012): 192-201.) investigated the effect of oat products on type 2 diabetes in an animal model.

In the course of the present invention, various ingredients, formulations, or production process were tested in particular for their efficacy in skin disorders or diseases. Ultimately, the preparation according to the invention proved to be particularly effective for the treatment of skin disorders (in particular with a *papaya* component, as described further below, see also example 2).

Surprisingly, it was found in the course of the present invention that by the addition of a preparation of *carica papaya* fruit (Component A), preferably a puree preparation from *carica papaya* fruit, to the, preferably boiling, slurry, an increase in the avenanthramide concentration in relation to the dry mass of oat flour can be achieved (see example 4). Accordingly, the addition of Component A to a final proportion of 20% of the total dry mass, resulted in an increase of the avenanthramide concentration by 10% with respect to the oat flour dry mass. This could be explained by the fact that components of *papaya* activate or stabilize the HHT enzyme, resulting in an increased transformation into avenanthramides.

*Carica papaya* (melon tree) belongs to the family of caricaceae violales and produces large, juicy, and palatable fruit (papayas).

The *papaya* is native to tropical regions, where it was also cultivated. Large-scale plantations are found in Ceylon, Pakistan, India, Australia, East Africa, and Brazil. Just as many plantations are found in Mexico and Central America, which are much smaller, however. The tree grows up to six meters high, and the fruit can reach a weight of up to 7 kg.

In traditional medical cultures, *papaya* (peel, pulp, seeds, rarely leaves and latex) is primarily used to treat asthma, parasitoses, wound healing disorders, as well as gastrointestinal problems, such as diarrhea or constipation. The ingredients stimulate and regulate digestive activity, mitigate gastric hyperacidity, reduce excessive gas formation, and support the breakdown of proteins.

Possible healing effects were first reported in writing by the Spaniard, Oviedo (1526). Dr. Mario Rojas Alba, President of the Mexican Institute for Traditional Medicine, has been extensively investigating the healing properties of this fruit since 1996.

So far, six different enzymes have been isolated: papain, chymopapain A and B, lysozyme, lipase, glutamine cyclopherase, kailose.

Furthermore, the *papaya* is a very good source of: pectin, vitamin A, B and C, essential fatty acids, bioflavonoids, potassium, calcium, magnesium, phosphatides, peptides, amino acids (e.g., arginine).

Glycoside carpain is said to have a strengthening effect on the heart muscle.

In addition to the use as food, the fruit of *carica papaya* is used to produce the proteolytic enzyme, papain.

Papain was used to prevent burns infections, for the defibrination of wounds, to treat insect bites, for the treatment of edema, inflammatory processes, and to accelerate wound healing, as well as—in small doses—for stomach upsets. Papayas are further described as laxative and refreshing.

Papain (*papaya* peptidase I, EC 3.4.22.2) is obtained from the milky juice (latex) of unripe papayas, by drying and pulverizing the latex.

Both, *papaya* preparations and oatmeal preparations, through their many positive attributes, are in principle suitable for internal and external use in humans and animals.

Due to all the mentioned benefits, in particular the beneficial effect on the avenanthramide concentration, a preferred embodiment of the method according to the invention further comprises:

d) adding a preparation of *carica papaya* fruit (Component A), preferably a puree of *carica papaya* fruit, to the preferably boiling slurry (Component B).

Preferably this method step is characterized in that the addition of Component A takes place with stirring and/or up to a total concentration of Component A of 5%-50% (v/v), preferably 10%-40% (v/v), most preferably 15%-25% (v/v).

A commercially successful use of a puree preparation of *papaya* fruit is disclosed in WO 2004/047850 A1. It is a preparation that may have higher effectiveness than conventional *papaya* preparations due to the special production method (hereinafter also called the special puree preparation", the special *papaya* puree preparation", "the special puree preparation of *carica papaya* fruit," or "the special *papaya* preparation"). It is helpful, among others, for digestive disorders.

Until now, use of the special *papaya* puree preparation on the skin has not been known. In the course of the present invention, the suitability of the preparation of this invention (comprising the special *papaya* puree preparation) was tested for use to treat inflammatory disorders of the skin. The preparation according to the invention (comprising special

*papaya* puree preparation), proved to be particularly suitable, especially because of the anti-inflammatory and soothing effects of the *papaya* preparation, which is complemented by the oat flour component (e.g., the avenanthramides contained therein), and with which the viscosity of the preparation can be controlled well (and thus improved), which is very important for application to the skin. A beneficial effect on the avenanthramide concentration can also be observed.

Therefore, a preferred embodiment of the method according to the invention is characterized in that Component A is a puree preparation of *carica papaya* fruit ("the special *papaya* puree preparation"), obtainable by a method characterized by the steps of:
 boiling the fruit or crushed fruit, in particular fruit in sieved form, for at least 30 minutes at normal pressure, optionally with at least twice the volume of an aqueous solution,
 cooling the boiled fruit or crushed fruit for a period of at least 30 minutes under an atmosphere containing oxygen, preferably under supply of air and at room temperature,
 optionally crushing, mixing, and straining the cooled fruit or crushed fruit until a homogenous puree is obtained.

In particular, the combination of active ingredients of the special *papaya* puree preparation and the oat flour is of outstanding importance for the therapeutic properties of the present invention. Therefore, the special manufacturing process multiplies the positive effect of the *papaya* fruit on the skin and/or mucous membranes as well as improving the well-known antibacterial, antifungal, and anti-inflammatory effect of the oats. In summary, the preparation according to the invention can comprise, among others, the following characteristics and effects: UV absorbing, cleansing effect (due to the *papaya* puree preparation), immune-regulating, ceramide synthesis-stimulating, moisturizing (due to the oat flour), anti-inflammatory, analgesic, anti-oxidative, wound-healing, itch-reducing, and irritation-reducing (by the coaction of both components). The preparation according to the invention can be used during pregnancy and lactation period and is also suitable for babies and toddlers.

CN 102406042 A discloses an ice cream for weight loss with *papaya* and oats (i.e., oatmeal or oat grains, but not oat flour!) Therefore, the document does not anticipate the present invention, nor could the present invention be derived from it.

CN 103519078 A discloses a pastry from *papaya* juice and oatmeal. In particular, the boiling time of a slurry containing oat is not disclosed, however. Furthermore, we must distinguish between *papaya* juice and *papaya* puree, as will be explained later in the present description. Therefore, the document does not anticipate the present invention, nor could the present invention be derived from it.

CN 102524640 A discloses a powder for colon cleansing, containing, among other, oatmeal and *papaya*. In particular, a boiling step is not disclosed, however. Therefore, the document does not anticipate the present invention, nor could the present invention be derived from it.

There may indeed be known a variety of home remedies or the like in which *papaya* puree and rolled oats (perhaps also oat flour) are combined, mainly before the application, for example, for application to the skin, but the present invention differs in one or more of the following aspects:
 In the present invention, the activity of the ingredients, especially of the papain contained in Component A, is particularly well preserved.
 In the present invention, the pH can be lowered to a very compatible level (for example, for the skin or mucosa) by the addition of lemon juice concentrate or another comestible acidifying agent.
 In the present invention, oat flour is used (rather than rolled oats), resulting firstly in better extraction of the active ingredients and, secondly, in a more uniform consistency. In addition, oat flour contains more folic acid compared to rolled oats, as per:
 http://www.ernaehrung.de/lebensmittel/de/C233000/Hafer-Mehl.php und
 http://www.ernaehrung.de/lebensmittel/de/C133000/Hafer-Flocken.php
 Folic acid is effective against chronic inflammatory skin diseases, such as psoriasis (Gisondi et al, J Dermatolog. Treat. 2007, PMID: 17538801, abstract).
 In the present invention, the slurry of oat flour is preferably boiled with constant stirring, improving the suitability of the invention for industrial use because, among other things, the viscosity can be controlled particularly well and the method of the invention also has hygienic advantages due to the boiling, for example in terms of shelf life. Home remedies, however, are usually designed to be prepared immediately before use. Therefore, they are not suitable for large-scale production of a commercial product.
 Oftentimes, only *papaya* juice (i.e., without pulp) is used in the prior art, rather than *papaya* puree. This results in the loss of many valuable ingredients. Embodiments of the preparation according to the invention, however, provide for the addition of *papaya* puree (i.e., with pulp).

The effects of the preparation according to the invention to achieve the skin improvements, demonstrated in the present invention, can be attributed to its soothing, anti-inflammatory, analgesic, and moisturizing effect, as well as its positive effects on wound healing.

The preparation according to the invention is characterized by controlled and uniform viscosity and hygienic advantages (among others, due to the boiling), for example, in terms of shelf life.

Heating and boiling can be carried out, for example, in a double boiler with a closed-circuit heater for better temperature control. During the cooling process, the supply of oxygen is important. The process is preferably carried under normal pressure or in the presence of air, in particular under supply of air.

Component A in itself is already disclosed in WO 2004/047850 A1, along with a detailed disclosure of the production method, the product characteristics, and the application. Likewise, the teachings of WO 2004/047850 A1 offer a concrete exemplary embodiment of a production method for Component A.

In a further preferred embodiment, the method according to the invention may further comprise one or more of the following steps:
 e) adding water (allows for adjusting the viscosity to improve the preparation), preferably after step c) or d), preferably up to a total water content (v/v) of the preparation between 75% and 95%, preferably between 80% and 93%, most preferably between 85% and 90%;
 f) maintaining the mixture at 70° C.-90° C., in particular 75° C.-85° C., for at least 10 minutes; (allows for, among others, particularly good mixing under hygienic conditions), preferably after steps c) or d) or e);
 g) adding (a) binder agent(s) (allows for adjusting the viscosity), (a) flavoring agent(s) (may make the product more palatable for the patient or consumer), and/or (a) preservatives(s), preferably after steps c) or d) or e) or f);

h) adjusting the pH to between 4 and 6, preferably 4.5 to 5.5, by addition of lemon juice concentrate, citric acid and/or another comestible acidifier (especially important, among others, for application to the skin as a slightly acidic pH value corresponds to the physiological pH value of the skin and may be important for a good shelf life of the product), preferably after steps c) or d) or e) or f) or g).

The respective boiling steps for the *papaya* or oats component according to the method according to the invention must be carried out for at least 30 minutes, since only insufficient extraction can be achieved otherwise. Preferably, the respective boiling step is carried out independently, but for at least one hour, more preferably for at least two hours, most preferably for at least three hours. In particular, the oats boiling step is carried out for at least 30 minutes, preferably for at least 45 minutes, more preferably for at least 1 hour, even more preferably for at least 2 hours, most preferably for at least 3 hours; this serves, among others, to increase the avenanthramide concentration. In further embodiments, the oats boiling step is carried out for at least 4 hours, preferably for at least 5 hours, more preferably for at least 6 hours, even more preferably for at least 8 hours, most preferably for at least 10 hours. For technical reasons, it is recommended to not necessarily carry out the respective boiling step for the *papaya* or oats component for more than 24 hours, preferably not longer than 12 hours, most preferably not more than 8 hours, and then—in the case of the *papaya* component—allow the component to cool to room temperature. The cooling step is preferably carried out at room temperature (20° C.) and normal pressure in a normal atmosphere until the preparation is cooled down to at least 40° C., in particular at least 30° C.

According to a preferred embodiment, the present invention in a further aspect relates to a preparation obtainable according to the method according to the invention, wherein the oat flour is preferably used as an aqueous colloid. In particular with thorough mixing (for example by particularly prolonged stirring time), the substantially largest proportion of oat flour is present as a colloid. If the oat flour is finely ground oat flour (optionally having an average particle diameter of less than 2000 µm, preferably less than 1500 µm, more preferably less than 1000 µm or even 500 µm), it particularly supports the colloid formation and results in a particularly homogeneous consistency, including a uniform viscosity. For not perfectly spherical particles, "diameter" is to be understood to mean the length of the longest dimension of the particles. Preferably, the oat flour used in the invention substantially contains no (e.g., less than 0.1% of) particles larger than 5000 µm, more preferably substantially no particles larger than 2000 µm, in particular substantially no particles larger than 500 µm.

Although, for the reasons stated herein, the preparation according to the invention with the special *papaya* puree is excellently suited to fulfill the objects of the invention, another embodiment of the preparation according to the invention, in which the *papaya* preparation is added or prepared in other ways than those previously mentioned, is also suited to fulfill the objects of the invention.

In a further preferred embodiment of the present invention, the preparation is hygienic as a result of the boiling. "Hygienic" preferably means that the preparation does not exceed the European or Austrian tolerance values or limits for germ load in food or food supplements. In particular, hygienic means that less than 1000000 colony forming units (CFU) of mesophilic, aerobic bacteria are present per gram of the preparation, preferably less than 100000 CFU per gram, more preferably less than 10000 CFU per g, even more preferably less than 1000 CFU per g.

In a further preferred embodiment of the present invention, the preparation is characterized in that the concentration of the avenanthramides in relation to the total dry mass of the preparation is at least 500 ppm, preferably at least 1000 ppm, more preferably at least 1250 ppm, even more preferably at least 1500 ppm, most preferably at least 1750 ppm;

preferably wherein the avenanthramide B is a component of said avenanthramides, preferably of at least 5%, more preferably at least 10%, even more preferably of at least 20%, most preferably more than 50% or even more than 75%.

In a further preferred embodiment, the preparation according to the invention also includes lemon juice concentrate, preservatives, starch, flavoring(s) and/or water, optionally without further ingredients. The term "without further ingredients" in the context of the present application means that these further ingredients are included only in negligible traces, if at all, for example in a concentration of less than 1 or 10 or 100 ppm (parts per million).

The ingredients mentioned above can improve the suitability of the preparation as a commercial product, for example through a quality structure that is optimized for the possible applications (e.g., in terms of viscosity and pH), longer shelf life, optionally while maintaining quality structure, and properties that are attractive to the user (with respect to color, odor, taste, consistency, etc.).

In a further preferred embodiment, the total concentration (v/v) of starch and preservatives in the preparation according to the invention are each independently between 0% and 2%, in particular between 0.5% and 1.5%. Preferably, the preparation according to the invention is pasteurized by methods known in the art. This results, among others, in an improvement of the viscosity and shelf life.

In a further preferred embodiment, the preparation according to the invention is characterized in that the water content (v/v) of the preparation is between 75% and 95%, preferably between 80% and 93%, most preferably between 85% and 90%. This results in an improvement of viscosity and handling of the preparation.

In a further preferred embodiment, the preparation according to the invention is characterized in that the pH of the preparation is between 4 and 6, in particular between 4.5 and 5.5. This is useful for improving the compatibility of the preparation when applied to the skin or mucous membrane, when ingested, etc.

In a further preferred embodiment, the preparation according to the invention is characterized in that the viscosity of the preparation is between 3000-10000 cP (Centipoise), in particular between 4000 and 8000 cP. This results in an improvement the handling of the preparation.

In a further preferred embodiment, the preparation according to the invention is characterized in that the puree preparation (particularly for the special *papaya* puree preparation) is made from *carica papaya* fruit:

boiling is carried out for at least 2 h; and/or
cooling is carried out for at least 5 h; and/or
the fruit is peeled and cored before boiling; and/or
the fruit is half-ripe to ripe;
and/or the puree preparation of *carica papaya* fruit is pasteurized.

This results in a further increase in the activity of the ingredients (including papain activity) in the puree preparation of *carica papaya* fruit. The best results can be achieved with *carica papaya* fruit that is half-ripe to ripe. The ripeness of the papayas may be defined by the color of the skin: Unripe fruit has 100% green skin, half-ripe fruit is 50-75% yellow, and ripe fruit is 80-100% yellow. In order to obtain a final product that looks even more appetizing in its consistency and form and can be ingested even better, the fruit may be peeled and cored before the boiling process. This opportunity can be used to crush the fruit even before the boiling process, for example by sieving. Subsequent pasteurization of the obtained puree under conventional food technological conditions may also be preferred.

Another aspect of the present invention relates to the use of the preparation according to the invention in therapeutic and/or cosmetic methods.

A preferred embodiment of this aspect relates to the preparation according to the invention for use in therapeutic methods.

According to the invention, the preparation may be used in the treatment of irritated and/or inflammatory conditions of the skin (or mucosa), selected from dermatitis, especially atopic dermatitis, itching, redness, dry, cracked, open, oozing, thickened, inflamed skin or mucosa, sunburn, insect bites, and psoriasis, and be characterized in that the application is preferably carried to the skin or mucosa, especially directly at the site of irritated and/or inflammatory conditions.

The preparation according to the invention, in particular when applied externally against itching and/or redness of the face and body, can be used for dry, irritated, sensitive, young, and mature skin.

Furthermore, the preparation according to the invention can be used for the treatment of digestive disorders, preferably selected from the group consisting of chronic constipation, flatulence, gastritis, heartburn, and irritable bowel syndrome, preferably characterized in that the preparation is administered orally. As mentioned above, both, *papaya* fruit pulp and oat flour, are excellently suited for consumption.

In addition, the preparation according to the invention in a further embodiment can be used in the treatment of one or more diseases or conditions, selected from:
- weakened immune system (where the immune system is strengthened)
- wounds, especially for ulcus cruris,
- diabetes (where insulin resistance is decreased in patients with type 2 diabetes, resulting in an improvement of the disease pattern).

As part of such treatment methods, the preparation according to the invention is administered to the patient in an effective amount, wherein the patient preferably already suffers from a diagnosed medical condition that requires the treatment according to the invention or is (or is assumed to be) at risk of having or developing such a disease.

A further aspect of the present invention relates to a cosmetic method for use of the preparation according to the invention, preferably to the skin, to achieve a beautiful appearance of the skin. It can be used, among others, to treat blemished skin and/or compensate for irregular pigmentation of the skin.

Other Definitions:

The term "flavorings" includes all "flavoring substances" recognized in the database of the European Union (http://ec.europa.eu/food/food/chemicalsafety/flavouring/database/) as well as in the Implementing Regulation (EU) No. 872/2012 of the Commission of Oct. 1, 2012, laying down the list of flavoring substances named in Regulation (EC) No. 2232/96 (http://eur-lex.europa.eu/LexUriServ/LexUriServ.do?uri=OJ:L:2012:267:0001:0 161:DE:PDF).

The term "preservative" includes all preservatives approved in the European Union, among others, substances with the following E-numbers (according to the list of food additives approved in the European Union): 200, 202, 203, 210, 211, 212, 213, 214, 215, 218, 219, 220, 221-228, 232, 231, 232, 234, 235, 239, 242, 249, 250, 251, 252, 260-263, 270, 280-285, 290, 296, 297, 1105.

The term "comestible acidifying agent" includes all acidic food ingredients approved in the European Union, in particular substances with the following E-numbers (according to the list of food additives approved in the European Union): E260, E270, E290, E296, E296, E330, E334, E338.

The term "binder" includes all gelling agents, thickening agents, or binders approved in the European Union, preferably substances with the following E-numbers (according to the list of food additives approved in the European Union): E400-E499, in particular xanthan (E415).

The term "boiling" means first and foremost holding the product to be boiled at a temperature equal to or above 100° C., in particular at a temperature of substantially 100° C. (at normal pressure, at sea level). It will be apparent to those skilled in the art, however, that even boiling temperatures below 100° C., at normal pressure, at sea level, is within the context of the present invention, as long as it is compatible with the term "boiling" to those skilled in the art. In particular, these temperatures (at atmospheric pressure, at sea level) are above 80° C., preferably above 85° C., more preferably above 90° C., even more preferably above 95° C. However, for hygienic reasons alone, a boiling temperature equal to or above 100° C. (at normal pressure, at sea level), in particular of substantially 100° C. (at normal pressure, at sea level), is most preferred.

Of course, it will be apparent for those skilled in the art that the temperature may rise above, or fall bellow, the respective boiling temperature during boiling for a certain period or time (e.g., 20%, 10%, or 5% of the boiling time) as long as the temperature averaged over the boiling time is equal to the prescribed boiling temperature. However, it is preferred that the temperature during cooking is substantially constant, in particular substantially constant at equal to or above 100° C., in particular at a constant temperature of substantially 100° C. (at normal pressure, at sea level).

Although avenanthramides, for example, (and other ingredients) are generally resistant to heat, it can nevertheless be indicated for the stability of certain ingredients (e.g., avenanthramide B) during boiling to exceed a temperature of 150° C., more preferably 125° C., even more preferably 100° C., only briefly, if at all, preferably not longer than 20% of the boiling time, more preferably not longer than 10% of the boiling time, even more preferably not longer than 5% of the boiling time, most preferably not at all during the boiling time.

The term "water" in the present invention is understood in the sense common in the treatment of oat flour or for the preparation of oat flour products and therefore, besides the pure water types used in the customary manner in the pharmaceutical field, such as distilled or deionized water, also comprises tap water or water containing electrolytes, as well as water that contains the additives common for the preparation of, in particular, dietetic oat flour products.

The term ppm means "parts per million." With respect to avenanthramides, ppm is calculated by: avenanthramid mass [μg]/total dry mass [g]=avenanthramide concentration [ppm].

A preparation of X is defined as comprising all types of preparation, production as well as processed forms of X.

A puree from a fruit by definition includes the pulp (fruit flesh) of the fruit, while a juice is filtered from a fruit and does not include the pulp or is lacking substantial portions thereof.

It is evident to those skilled in the art that the "stirring" as part of the process of the invention can be replaced entirely or in part by other means of mechanical agitation, provided they can essentially be considered as technically equivalent. It is preferred, however, that the "stirring" within the scope of the method according to the invention is carried out as actual stirring.

All documents from the prior art referenced herein shall be included by reference in the present description.

The invention is further illustrated referring to the following embodiments, to which it is of course not limited:

1. A method of making a preparation from oat flour, comprising:
   a) suspending the oat flour in preferably cold water;
   b) heating the slurry, preferably with stirring, to boiling temperature;
   c) boiling the slurry with stirring for at least 30 minutes, preferably for at least 45 minutes, more preferably for at least 1 hour, even more preferably for at least 2 hours, most preferably for at least 3 hours;
   the oat flour having a mean particle diameter of less than 2000 μm, preferably less than 1500 μm, more preferably less than 1000 μm, even more preferably less than 500 μm, and most preferably less than 350 μm.
2. The method according to claim 1, further comprising
   d) adding a preparation of *carica papaya* fruit (Component A), preferably a puree of *carica papaya* fruit, to the preferably boiling slurry (Component B)
   preferably characterized in that the addition of Component A takes place with stirring and/or up to a total concentration of Component A of 5%-50% (v/v), preferably 10%-40% (v/v), most preferably 15%-25% (v/v).
3. The method according to embodiment 2, wherein Component A is a puree preparation of *carica papaya* fruit, obtainable by a method characterized by the steps of:
   boiling the fruit or crushed fruit, in particular fruit in sieved form, for at least 30 minutes at normal pressure, optionally with at least twice the volume of an aqueous solution,
   cooling the boiled fruit or crushed fruit for a period of at least 30 minutes under an atmosphere containing oxygen, preferably under supply of air and at room temperature,
   optionally crushing, mixing, and straining the cooled fruit or crushed fruit until a homogenous puree is obtained.
4. The method according to any one of embodiments 1 to 3, further comprising one or more of the steps of:
   e) adding water;
   f) maintaining the mixture at 70° C.-90° C., in particular 75° C.-85° C., for at least 10 minutes;
   g) adding binder(s), flavoring(s) and/or preservative(s);
   h) adjusting the pH to between 4 and 6, preferably 4.5 to 5.5, by addition of lemon juice concentrate, citric acid and/or another comestible acidifier.
5. A preparation, obtainable by a method according to any one of the embodiments 1 to 4, preferably wherein the preparation is hygienic as a result of boiling and/or preferably wherein the oat flour is present as an aqueous colloid.
6. The preparation according to embodiment 5, wherein the concentration of the avenanthramides in relation to the total dry mass of the preparation is at least 500 ppm, preferably at least 1000 ppm, more preferably at least 1250 ppm, even more preferably at least 1500 ppm, most preferably at least 1750 ppm.
7. The preparation according to embodiment 5, wherein the concentration of avenanthramide B in relation to the total dry mass of the oat flour in the preparation is at least 1000 ppm, preferably at least 1500 ppm, more preferably at least 1750 ppm, even more preferably at least 2000 ppm, most preferably at least 2250 ppm.
8. The preparation according to any one of the embodiments 5 to 7, further comprising lemon juice concentrate, preservatives, starch, flavoring(s) and/or water, optionally without further ingredients.
9. The preparation according to any one of the embodiments 5 to 8, characterized in that the total concentrations (v/v) of starch and preservatives are each independently between 0% and 2%, in particular between 0.5% and 1.5%, and optionally characterized in that it is pasteurized.
10. The preparation according to any one of the embodiments 5 to 9, characterized in that the water content (v/v) of the preparation is between 75% and 95%, preferably between 80% and 93%, most preferably between 85% and 90%.
11. The preparation according to any one of the embodiments 5 to 10, characterized in that the pH of the preparation is between 4 and 6, in particular between 4.5 and 5.5.
12. The preparation according to any one of the embodiments 5 to 11, characterized in that the viscosity of the preparation is between 3000 and 10000 cP, in particular between 4000 and 8000 cP.
13. The preparation according to any one of the embodiments 5 to 13, containing the puree preparation of *carica papaya* fruit, obtainable by a method, the method further characterized in that:
    boiling is carried out for at least 2 h; and/or
    cooling is carried out for at least 5 h; and/or
    the fruit is peeled and cored before boiling; and/or
    the fruit is half-ripe to ripe;
    and/or the puree preparation of *carica papaya* fruit is pasteurized.
14. The preparation according to any one of the embodiments 5 to 13, for use in therapeutic methods.
15. The preparation according to embodiment 14, for use in the treatment of irritated and/or inflammatory conditions of the skin (or mucosa), selected from:
    dermatitis, especially atopic dermatitis, itching, redness, dry, cracked, open, oozing, thickened, inflamed skin or mucosa, sunburn, insect bites, and psoriasis,
    characterized in that the application is preferably carried to the skin or mucosa, especially directly at the site of irritated and/or inflammatory conditions.
16. The preparation according to embodiment 14, for use in the treatment of digestive disorders, preferably selected from the group consisting of chronic constipation, flatulence, gastritis, and irritable bowel syndrome, characterized in that the preparation is administered orally.
17. The preparation according to embodiment 14, for use in the treatment of one or more diseases or conditions, selected from:
    weakened immune system
    wounds, especially for ulcus cruris,
    diabetes.

18. A cosmetic method, comprising the application of the preparation according to any one of the embodiments 5 to 13, preferably to the skin, to achieve a more beautiful skin appearance.

19. A method for increasing the content of avenanthramide, in particular avenanthramide B, in an oat flour product, characterized in that oat flour with an average particle diameter of less than 2000 μm, preferably less than 1500 μm, more preferably less than 1000 μm, even more preferably less than 500 μm, and most preferably less than 350 μm, is slurried in water for at least 30 minutes, preferably for at least 45 minutes, more preferably for at least 1 hour, more preferably for at least 2 hours, most preferably for at least 3 hours; is subjected to a boiling step.

20. The method according to embodiment 19, wherein the oat flour used in the invention substantially contains no (e.g., less than 0.1% of) particles larger than 5000 μm, more preferably substantially no particles larger than 2000 μm, in particular substantially no particles larger than 500 μm.

21. Use of a boiling step for at least 30 minutes, preferably for at least 45 minutes, more preferably for at least 1 hour, even more preferably for at least 2 hours, most preferably for at least 3 hours, for increasing the content of avenanthramide, in particular avenanthramide B, in an oat flour product.

Moreover, the invention is further illustrated referring to the following embodiments, to which it is of course not limited:

A1. A method of making a preparation from *carica papaya* fruit and oat flour, comprising:
a) suspending the oat flour in preferably cold water (Component B);
b) heating the slurry to boiling temperature with stirring;
c) boiling the slurry with stirring, preferably for at least 30 minutes, most preferably for at least 3 hours;
d) adding a puree preparation of *carica papaya* fruit (Component A*) to the preferably boiling slurry, wherein Component A* is obtainable by a method, characterized by the following steps:
  boiling the fruit or crushed fruit, in particular fruit in sieved form, for at least 30 minutes at normal pressure, optionally with at least twice the volume of an aqueous solution,
  cooling the boiled fruit or crushed fruit for a period of at least 30 minutes under an atmosphere containing oxygen, preferably under supply of air and at room temperature,
  optionally crushing, mixing, and straining the cooled fruit or crushed fruit until a homogenous puree is obtained, preferably characterized in that the addition of Component A* takes place with stirring and/or up to a total concentration of Component A* of 5%-50% (v/v), preferably 10%-40% (v/v), most preferably 15%-25% (v/v).

A2. The method according to embodiment A1, further comprising one or more of the steps of:
e) adding water;
f) maintaining the mixture at 70° C.-90° C., in particular 75° C.-85° C., for at least 10 minutes;
g) adding binder(s), flavoring(s) and/or preservative(s);
h) adjusting the pH to between 4 and 6, preferably 4.5 to 5.5, by addition of lemon juice concentrate, citric acid and/or another comestible acidifier.

A3. A preparation obtainable by a method according to embodiment A1 or A2, wherein the oat flour is preferably present as an aqueous colloid.

A4. A preparation from *carica papaya* fruit and oat flour, comprising:
A) a puree preparation of *carica papaya* fruit, obtainable by a method characterized by the steps of:
  boiling the fruit or crushed fruit, in particular fruit in sieved form, for at least 30 minutes at normal pressure, optionally with at least twice the volume of an aqueous solution,
  cooling the boiled fruit or crushed fruit for a period of at least 30 minutes under an atmosphere containing oxygen, preferably at room temperature,
  optionally crushing, mixing, and straining the cooled fruit or crushed fruit until a homogenous puree is obtained; and
B) oat flourj, preferably as an aqueous colloid.

A5. The preparation according to embodiments A3 to A4, further comprising lemon juice concentrate, preservatives, starch, flavoring(s) and/or water, optionally without further ingredients.

A6. The preparation according to any one of the embodiments A3 to A5, characterized in that the total concentrations (v/v) of starch and preservatives are each independently between 0% and 2%, in particular between 0.5% and 1.5%, and optionally characterized in that it is pasteurized.

A7. The preparation according to any one of embodiments A3 to A6, characterized in that the water content (v/v) of the preparation is between 75% and 85%, in particular between 78% and 82%.

A8. The preparation according to any one of embodiments A3 to A7, characterized in that the pH of the preparation is between 4 and 6, in particular between 4.5 and 5.5.

A9. The preparation according to any one of the embodiments A3 to A8, characterized in that the viscosity of the preparation is between 5000 and 10000 cP, in particular between 6000 and 8000 cP.

A10. The preparation according to any one of the embodiments A3 to A9, characterized in that, in the puree preparation from *carica papaya* fruit:
boiling is carried out for at least 2 h; and/or
cooling is carried out for at least 5 h; and/or
the fruit is peeled and cored before boiling; and/or
the fruit is half-ripe to ripe;
and/or the puree preparation of *carica papaya* fruit is pasteurized.

A11. The preparation according to any one of the embodiments A3 to A10, for use in therapeutic methods.

A12. The preparation according to embodiment A11, for use in the treatment of irritated and/or inflammatory conditions of the skin (or mucosa), selected from:
dermatitis, especially atopic dermatitis, itching, redness, dry, cracked, open, oozing, thickened, inflamed skin or mucosa, sunburn, insect bites,
and psoriasis, and characterized in that the application is preferably carried to the skin or mucosa, especially directly at the site of irritated and/or inflammatory conditions.

A13. The preparation according to embodiment A11, for use in the treatment of digestive disorders, preferably selected from the group consisting of chronic constipation, flatulence, and irritable bowel syndrome, characterized in that the preparation is administered orally.

A14. The preparation according to embodiment A11, for use in the treatment of one or more diseases or conditions, selected from:
weakened immune system
wounds, especially for ulcus cruris,
diabetes.

A15. A cosmetic method, comprising the application of the preparation according to any one of the embodiments A1 to A 10, preferably to the skin, to achieve a more beautiful skin appearance.

The invention is further illustrated referring to the following figures and examples, to which it is of course not limited.

EXAMPLES

Example 1

Production of the Preparation According to the Invention

Organic oat flour with a maximum particle diameter of 1000 µm is slurried in cold water (Component B) in a double boiler equipped with a closed-circuit heater. With continuous stirring, the slurry is heated to 100° C., boiled for three hours at 100° C., and thereby thickened. The double boiler with closed-circuit heater ensures even temperature distribution and fast heating to the desired temperature. Moreover, the circulation method results in an accumulation of oxygen in the product.

As a quality characteristic, the pH, water content, and viscosity of the slurry are now determined (and possibly corrected), with the target parameters: pH 6-7, water content 85-90%, and viscosity 25000-30000 cP.

Then, the *papaya* fruit puree (Component A, known from WO 2004/047850 A1 and also described in the present application) is added to the boiling slurry with stirring up to a total concentration of 10-40% (v/v), after which the mixture is heated and maintained at 75-85° C. for 5-15 minutes with stirring.

As a quality characteristic, the pH, water content, and viscosity of the mixture are now determined (and possibly corrected), with the target parameters: pH 4.5-5.5, water content 75-95%, and viscosity 3000-10000 cP, wherein the pH is adjusted with organic lemon juice concentrate and the mixture is constantly maintained at 80° C.

Finally, the mixture (now the preparation according to the invention) at a temperature of 70-90° C. is filled in aseptic bags.

Example 2

Trial of the Preparation According to the Invention on Human Patients

Figure 1:
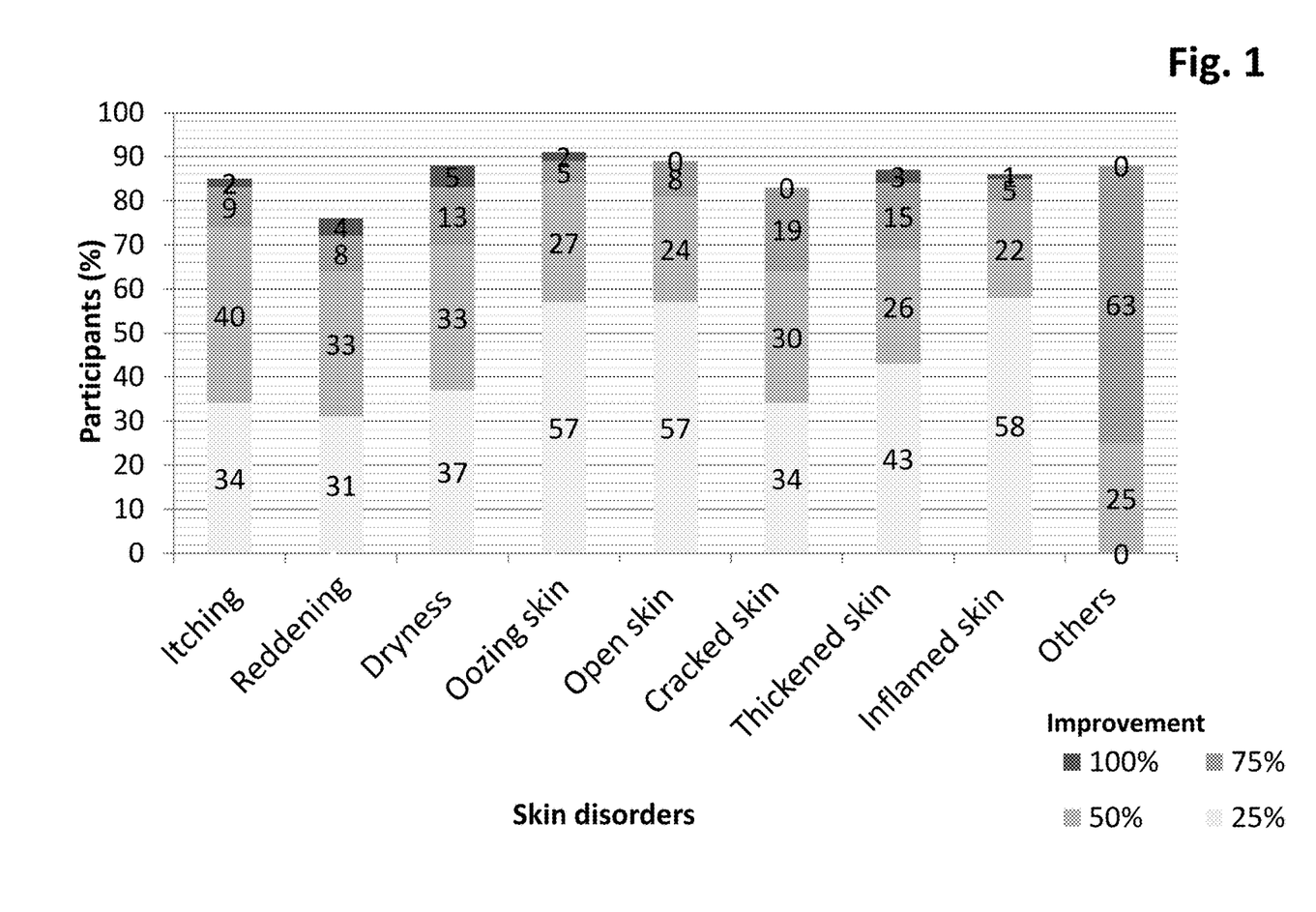
FIG. 1: Improvement in various skin disorders after application of the preparation of the present invention (Y-axis: percentage of subjects who had at least a 25% improvement after application), with an additional distinction made between a 25%, 50%, 75%, and 100% improvement.

The preparation of the present invention was tested in a pilot study with volunteer test subjects, where the preparation was applied to the skin of the test subjects. The severity of various skin disorders was evaluated before and after the application by the test subjects and the improvement in symptoms was analyzed after the test phase (FIG. 1). There was a significant improvement (for approx. 85% of test subjects) as a result of the use of the *papaya* oat preparation in the case of the skin disorders, itching, redness, dry, cracked/open, oozing, thickened, and/or inflamed skin.

Example 3

Trial of the Preparation According to the Invention

The anti-inflammatory effect of the preparation on the skin and/or mucous membrane is supported by the results of a study on the inflammatory marker, alpha-1 antitrypsin, which can be formed increasingly and detected in cases of mucosal irritation and/or mucosal inflammation. Use of the preparation resulted in a reduction of this inflammatory marker, indicating calming and healing of the mucosal changes.

Example 4

Measuring the Avenanthramide Concentration

The avenanthramide B concentrations was measured in four samples by means of an external avenanthramide B standard (sigma), using HPLC analysis and UV detection:

P0 . . . *Papaya* before preparation into fruit puree
P1 . . . *Papaya* fruit puree (the special *papaya* fruit puree)
H0 . . . oat flour before preparation
H1 . . . oat flour after preparation (the preparation according to the invention, without any *papaya* component)
HP1 . . . oat flour+*papaya* fruit puree after preparation (the preparation according to the invention, comprising the special *papaya* fruit puree). The ratio of dry mass oat flour:*papaya* fruit puree is 80:20.

Avenanthramide B is "5-Hydroxy-2-{[(2E)-3-(4-hydroxy-3-methoxyphenyl)-1-oxo-2-propenyl]amino}benzoic acid, N-[4'-Hydroxy-3'-methoxy-(E)-cinnamoyl]-5-hydroxyanthranilic"

Preparation of Samples:

The samples were extracted 2 times for 15 min with 20% v/v ethanol in an ultrasonic bath and then centrifuged at 14500 rpm. The supernatant was used directly for HPLC analysis.

0.44 mg of the reference substance, avenanthramide B (Sigma), was dissolved in 96% ethanol and then diluted to 10.0 ml with 20% ethanol.

HPLC Method

Column Atlantis T3 3.5 µm 4.6×150 mm
Mobile phase A: acetonitrile
 B: 1% phosphoric acid
Gradient

| Time | A % | B % |
| --- | --- | --- |
| 0 | 20 | 80 |
| 20 | 60 | 40 |
| 30 | 100 | 0 |
| 35 | 100 | 0 |
| 36 | 20 | 80 |

Figure 2:
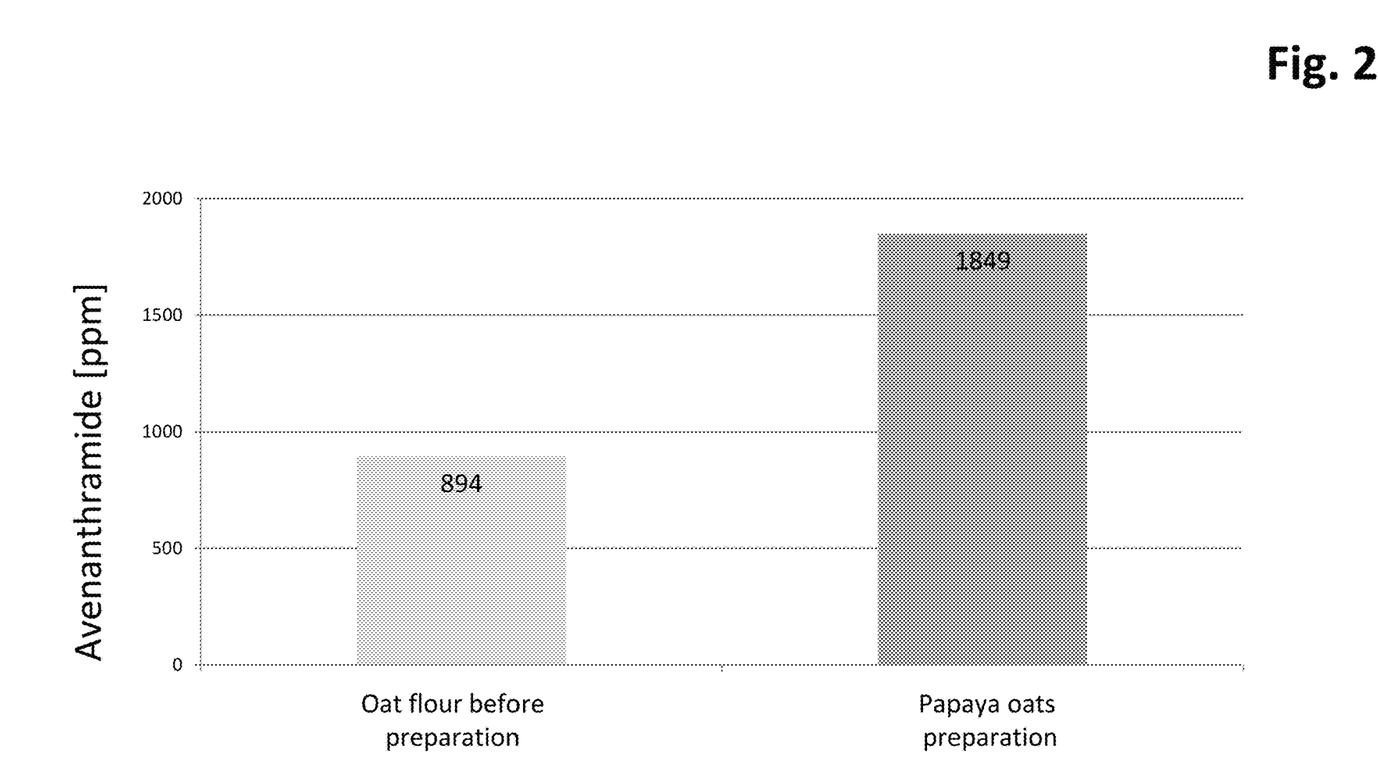
FIG. 2: Avenanthramide concentration (in ppm) in relation to the respective dry weight of oat flour prior to preparation ("H0"; i.e., prior to the method according to the invention) and the *papaya* oat preparation of the invention ("HP1"; i.e., the *papaya* oat preparation according to the invention, comprising the special *papaya* puree preparation; HP1).
Figure 3:
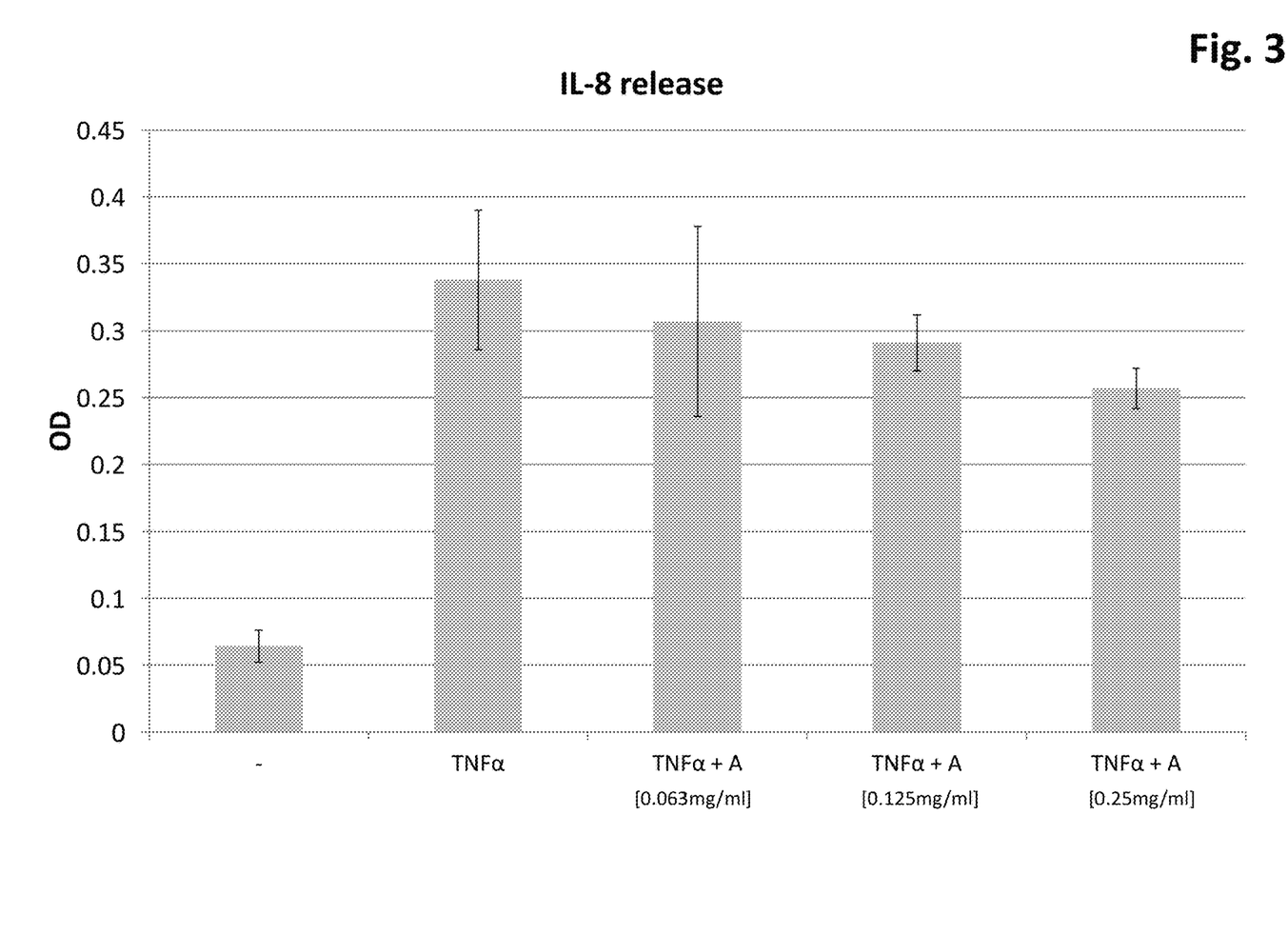
FIG. 3: The oat flour-*papaya* preparation (sample A) shows a dose-dependent inhibitory effect on the release of interleukin-8 (IL8) in human epidermal keratinocytes (HEKA). "–" is the negative control (no TNF-alpha), otherwise the TNF-alpha concentration is 10 ng/ml. OD: optical density.

Auto sampler time 41 min
Injection vol. Sample: 100 µl
Reference solution: 5 µl
UV detection 340 nm
Flow 0.5 ml/min
Results No avenanthramide B could be detected in the oat samples (H0, H1, HP1) (Tab. 1; FIG. 1-3). It was found that, in H1 (preparation according to the invention), a higher avenanthramide content was present than in H0 (oat flour before preparation). As expected, avenanthramide B could not be detected in P0 and P1.

TABLE 1

Avenanthramid contents based on dry mass

| Sample | Dry mass [%] | Avenanthramide B based on total dry mass [ppm] |
|---|---|---|
| P1 | 13.9 | not detectable |
| P0 | 9.7 | not detectable |
| H0 | 92.8 | 894 |
| H1 | 13.1 | 2069 |
| HP1 | 13.9 | 1849 |

The detection limit of the method was 0.044 ppm; the limit of determination was 0.1 ppm.

The measured concentrations of avenanthramides in the oat preparations studied here are sufficient to show the effects described above in a topical application.

The oat proportion in HP1 is only 80% of total dry mass. Based on the dry weight ratios between the oat and *papaya* component, the expected avenanthramide concentration is therefore 1655 ppm, rather than 1849 ppm (due to the dilution effect). Normalized to the oat dry mass, the avenanthramide concentration in HP1 is therefore 2311 ppm, which corresponds to a surprising increase of more than 10% compared to 2069 ppm of HP1.

It is therefore clear that the *papaya* component has a surprising beneficial effect in terms of the avenanthramide concentration of the oat component.

Example 5

Anti-Inflammatory Effect of the Preparation According to the Invention in Human Skin Epithelial Cells The anti-inflammatory effect of the oat flour *papaya* preparation was studied based on the effect of the preparation on the release of a pro-inflammatory cytokine, Interleukin-8 (IL-8) for tumor necrosis factor alpha–(TNF alpha–) stimulated skin epithelial cell cultures. Typically, stimulation of skin epithelial cells with TNF-alpha triggers the release of IL-8 by the skin epithelial cells, which in turn triggers or increases an inflammatory reaction.

Sample:
preparation of oat flour and *papaya* puree according to the present invention; Boiling time: 3 hours, mean oat flour particle diameter: 1000 µm, proportion of *papaya* (v/v): approx. 20%, total water content approx. 80% (v/v), pH 5. The sample is referred to as "Sample A" or "A" in this example.

Materials:
Human epidermal keratinocytes, adult (HEKa), Gibco®
"Human IL-8 ELISA development kit," PromoKine
"Cell Counting Kit-8," Dojindo Molecular Technologies
Human recombinant TNF-alpha, PromoKine
Dexamethasone, water-soluble, Sigma Methods:
Cytokine assay: Sample A was respectively added to several confluent cell cultures in cell culture medium to the specified concentration (0-0.25 mg/ml). The cell cultures were then pre-incubated in the incubator (37° C., 5% $CO_2$) for 30 minutes. Thereafter, TNF alpha was added to a concentration of 10 ng/ml and incubated for a further 24 hours. In addition, one cell culture was not incubated with TNF alpha (negative control). Thereafter, the respectively released concentration of IL-8 was tested with the "Human IL-8 ELISA development kit." Furthermore, the basic functioning of the assay was assured with the anti-inflammatory active ingredient, dexamethasone (as a positive control).

Cytotoxicity assay: Sample A was also tested for possible cytotoxicity. To this end, cell cultures were treated as in the cytokine assay; however, rather than the IL-8 concentration, the number of surviving cells was determined using the "Cell-Counting Kit-8," a tetrazolium salt-based colorimetric assay (similar to the "MTT assay").

Results:
Sample A was not cytotoxic at any of the concentrations studied. There was a dose-dependent inhibitory effect of sample A on the IL-8 release in human epidermal keratinocytes (FIG. 3). Therefore, an anti-inflammatory effect of the preparation according to the invention was confirmed in skin cells.

Example 6

Anti-Inflammatory Effect of the Preparation

According to the Invention in Human Intestinal Epithelial Cells (comparative example)

The anti-inflammatory effect of the preparation was studied based on the effect of the preparation on the release of a pro-inflammatory cytokine, Interleukin-8 (IL-8) for tumor necrosis factor alpha–(TNF alpha–) stimulated intestinal epithelial cell cultures. Typically, stimulation of intestinal epithelial cells with TNF-alpha triggers the release of IL-8 by the intestinal epithelial cells, which in turn triggers or increases an inflammatory reaction.

Samples:
Sample A: preparation of oat flour and *papaya* puree according to the present invention; Boiling time: 3 hours, mean oat flour particle diameter: 1000 µm, proportion of *papaya* (v/v): approx. 20%, total water content approx. 80% (v/v), pH 5.
Sample B: Preparation of oat flour, prepared according to the present invention; Boiling time: 3 hours, mean oat flour particle diameter: 1000 µm, proportion of *papaya* (v/v): 0%, total water content approx. 80% (v/v), pH 5.
Sample C: *Papaya* puree, as added to Sample A.

Materials:
Human intestinal epithelial cells, cell line HT29-MTX-E12 (ECACC)
"Human IL-8 ELISA development kit," PromoKine
"Cell Counting Kit-8," Dojindo Molecular Technologies
Human recombinant TNF-alpha, PromoKine
Dexamethasone, water-soluble, Sigma Methods:
Cytokine assay: Samples A, B, and C were added to several confluent cell cultures in cell culture medium to a concentrations of 1 mg/ml. The cell cultures were then pre-incubated in the incubator (37° C., 5% $CO_2$) for 30 minutes. Thereafter, TNF alpha was added to a concentration of 10 ng/ml and incubated for a further 24 hours. In addition, one cell culture was not incubated with TNF alpha (negative control). Thereafter, the respectively released concentration of IL-8 was tested with the "Human IL-8 ELISA development kit." Furthermore, the basic functioning of the assay was assured with the anti-inflammatory active ingredient, dexamethasone (as a positive control).

Figure 4:
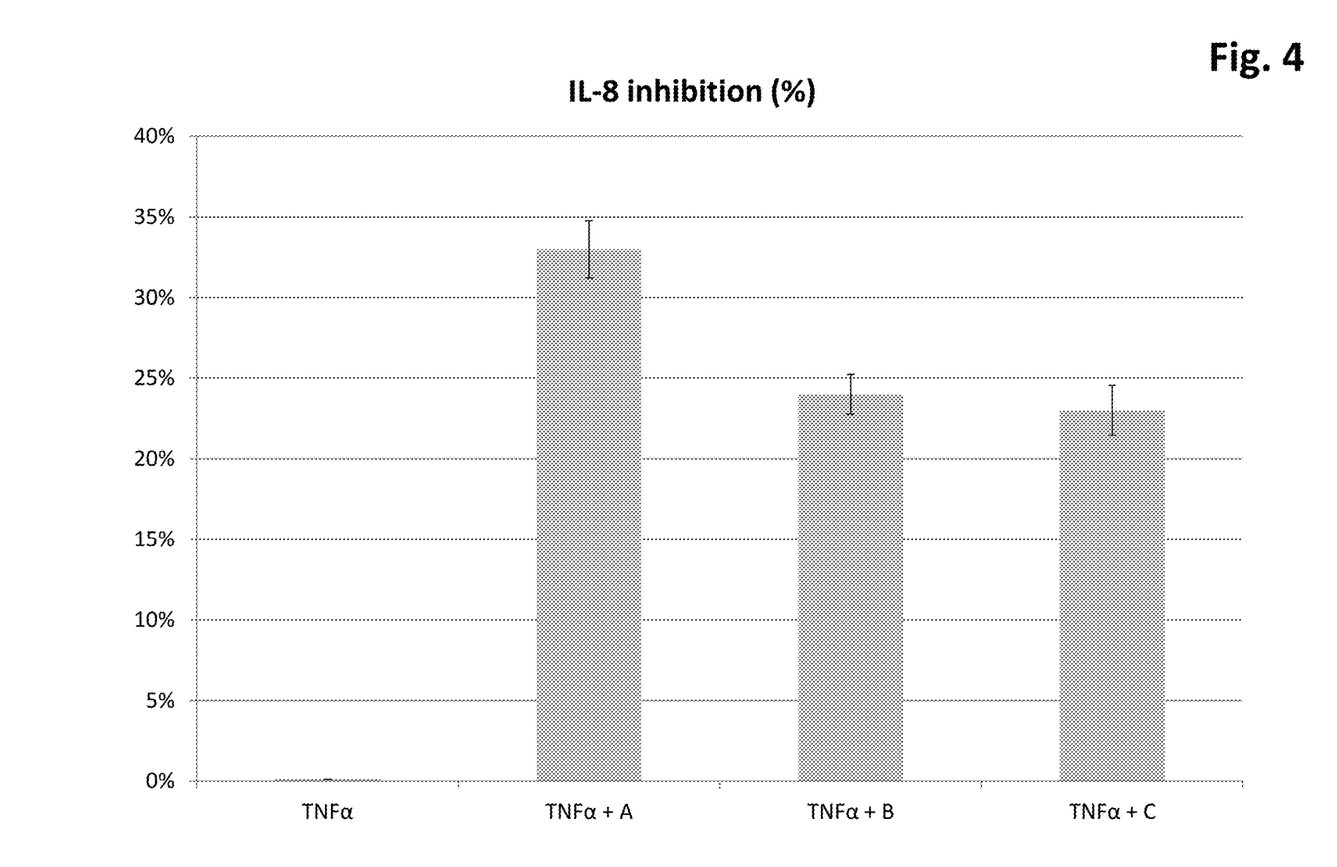
FIG. 4: The combination of oat flour and *papaya* in the preparation according to the invention surprisingly results in a synergistic inhibition of IL8 release in human intestinal epithelial cells (cell line HT29-MTX-E12). The figure shows the reduction in IL-8 concentration compared to the TNF-alpha control (10 ng/ml). A: preparation of oat flour and *papaya* puree (1 mg/ml), B: preparation of oat flour (1 mg/ml), C: *papaya* puree (1 mg/ml).

Cytotoxicity assay: Samples A, B, and C were also tested for possible cytotoxicity. To this end, cell cultures were treated as in the cytokine assay; however, rather than the IL-8 concentration, the number of surviving cells was determined using the "Cell-Counting Kit-8," a tetrazolium salt-based colorimetric assay (similar to the "MTT assay").
Results:

The samples A, B, and C were not cytotoxic at any of the concentrations studied. The combination of oat flour and *papaya* according to the invention demonstrated a synergistic inhibitory effect on IL-8 release (FIG. 4).

What is claimed is:

1. A method for preparing an anti-inflammatory therapeutic composition for treating skin or digestive disorders comprising the steps of:
   (a) suspending an effective amount of ground oats (Avena sativa) in water to produce a slurry, wherein the oat flour has a mean particle diameter of less than 1000 μm;
   (b) heating the slurry to boiling temperature (100° C.) with stirring;
   (c) boiling the slurry with stirring for at least 30 minutes;
   (d) adding an effective amount of a Carica papaya fruit puree to the boiling slurry to produce a mixture;
   (e) adding water to the mixture and maintaining temperature at 70 to 90° C. for at least 10 min;
   (f) adding binder(s), flavorings(s) and/or preservatives to the mixture; and
   (g) adding lemon juice concentrate, citric acid and/or another comestible acidifier to adjust the pH of the mixture to 4 to 6, to produce the therapeutic composition.

2. The method according to claim 1, wherein the carica papaya fruit puree is added in an amount of up to 50% v/v relative to the boiling slurry.

3. The method according to claim 1, wherein the carica papaya fruit is prepared by a method comprising:
   boiling the fruit or crushed fruit, in particular fruit in sieved form, for at least 30 minutes at normal pressure, optionally with at least twice the volume of an aqueous solution,
   cooling the boiled fruit or crushed fruit for a period of at least 30 minutes under an atmosphere containing oxygen, preferably under supply of air and at room temperature,
   optionally crushing, mixing, and straining the cooled fruit or crushed fruit until a homogenous puree is obtained.

4. The method according to claim 1, wherein the mean particle diameter of the oat flour is preferably less than 500 μm.

5. The method according to claim 1, wherein the mean particle diameter of the oat flour is less than 350 μm.

* * * * *